US012714386B2

(12) United States Patent
Dodson et al.

(10) Patent No.: US 12,714,386 B2
(45) Date of Patent: Aug. 25, 2026

(54) ANALYZING A PATIENT'S BREATHING BASED ON ONE OR MORE AUDIO SIGNALS

(71) Applicant: BROWN UNIVERSITY, Providence, RI (US)

(72) Inventors: Christopher M. Dodson, Providence, RI (US); Rashid Zia, Providence, RI (US); Christopher Rose, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 856 days.

(21) Appl. No.: 18/099,507

(22) Filed: Jan. 20, 2023

(65) Prior Publication Data

US 2023/0225695 A1 Jul. 20, 2023

Related U.S. Application Data

(60) Provisional application No. 63/301,073, filed on Jan. 20, 2022.

(51) Int. Cl.

| | |
|---|---|
| ***A61B 7/00*** | (2006.01) |
| ***A61B 5/00*** | (2006.01) |
| ***A61B 5/0205*** | (2006.01) |
| ***A61B 5/087*** | (2006.01) |

(52) U.S. Cl.

CPC ............ *A61B 7/003* (2013.01); *A61B 5/0205* (2013.01); *A61B 5/087* (2013.01); *A61B 5/6898* (2013.01); *A61B 5/7253* (2013.01); *A61B 5/7278* (2013.01); *A61B 2562/0204* (2013.01)

(58) Field of Classification Search

None

See application file for complete search history.

(56) References Cited

U.S. PATENT DOCUMENTS

| | | | | |
|---|---|---|---|---|
| 9,724,016 | B1 * | 8/2017 | Al-Ali | A61B 7/003 |
| 2015/0126888 | A1 * | 5/2015 | Patel | A61B 5/0871 600/538 |
| 2017/0112412 | A1 * | 4/2017 | Garbos | A61B 5/6898 |

OTHER PUBLICATIONS

Larson et al. (SpiroSmart: Using a Microphone to Measure Lung Function on a Mobile Phone; UbiComp' 12, Sep. 5-Sep. 8, 2012, Pittsburgh, USA) (Year: 2012).*

* cited by examiner

*Primary Examiner* — Jay B Shah

(74) *Attorney, Agent, or Firm* — Tarolli, Sundheim, Covell & Tummino LLP

(57) ABSTRACT

Audio signals, collected with equipment commonly available to individuals (e.g., a mobile device), can be used to analyze a patient's breathing. An audio signal associated with the patient's breathing for a time period can be detected with the mobile device and used to approximate the patient's respiratory flow for the time period. For example, the audio signal can be analyzed by determining a representation of an audio frequency of the audio signal, splitting the audio frequency of the audio signal into distinct time steps, determining points comprising a weighted mean frequency at each time step, applying a frequency-to-flow rate linear transformation at each time step to approximate the respiratory flow versus time, and plotting a graphical representation of the respiratory flow versus time. The respiratory flow for the time period can be tagged with a factor related to the patient and saved in a database for future analysis.

18 Claims, 6 Drawing Sheets

ANALYZING A PATIENT'S BREATHING BASED ON ONE OR MORE AUDIO SIGNALS

CROSS-REFERENCE TO RELATED APPLICATIONS

This application claims the benefit of U.S. Provisional Application Ser. No. 63/301,073, filed 20 Jan. 2022, entitled "A NOVEL METHOD OF USING AUDIO SIGNALS (BY THEMSELVES OR TOGETHER WITH CALIBRATING SENSOR READINGS) TO MEASURE RESPIRATORY HEALTH METRICS". The entirety of these applications is incorporated by reference for all purposes.

TECHNICAL FIELD

The present disclosure relates generally to respiratory function testing and, more specifically, to analyzing a patient's breathing based on audio signals, collected with a mobile device without requiring dedicated equipment, for respiratory function testing.

BACKGROUND

Spirometry is the most common pulmonary function test for measuring a patient's lung function. Spirometry can be used to diagnose and monitor conditions such as asthma, COVID-19, bronchitis, chronic obstructive pulmonary disease (COPD), cystic fibrosis, and pulmonary fibrosis. Spirometry is traditionally carried out in a doctor's office with a dedicated device called a spirometer, which commonly measures the amount of air a patient can breathe out in one second and the total volume of air the patient can exhale in one forced breath (represented in a respiratory flow curve). From the respiratory flow curve produced, factors can be extracted that can illustrate the patient's lung function including: vital capacity (VC), forced vital capacity (FVC), forced expiatory capacity (FEC), forced expiatory volume (FEV) at timed intervals of 0.5, 1.0, 2.0, and 3.0 seconds, forced expiatory flow 25%-75% (FEF 25-75), peak expiratory flow (PEF), maximal expiratory flow when X % remains ($MEF_x$), maximal mid-expiratory rate (MMEF), and maximal voluntary ventilation (MVV)/maximum breathing capacity, etc.). However, spirometry, and respiratory measurements in general, often relies on low resolution mechanical measurements or bulky and/or expensive hospital equipment, making a high level of data acquisition difficult. Moreover, traditional spirometry in the hospital setting requires significant user compliance with directions (e.g., cannot be used with young children, cannot be used with patients who cannot follow directions, cannot be used with patients who have one or more contraindications, etc.), may not accurately include the effects of environmental triggers (e.g., pollutants, asthma triggers, etc.), and may not accurately account for demographic factors (e.g., does not account for differences for different ethnicities, sexes, etc.). Additionally, spirometry often has a large cost, is not compact, and has a high user requirement for measurement, so any database for patients' lung function is quite small (often without data being tagged with a factor related to environmental, demographic, and/or clinical factors for further analysis) or does not exist.

SUMMARY

The present disclosure illustrates a low-cost and ubiquitous approach to analyze a patient's breathing in any setting using a mobile device. With the prevalence of mobile device ownership, there is a dense network of potential devices to provide large scale, high frequency measurements to one or more central databases, where the data can be tagged to enable the study of environmental, demographic, and/or clinical factors, including health factors, therapeutic factors, and the like. Achieving such respiratory function measurements will require minimal cost and low user requirement for measurement.

One aspect of the present disclosure is a mobile device for analyzing a patient's breathing based on audio signals for respiratory function testing. The mobile device can be associated with a microphone and can include a memory storing instructions; and a processor configured to access the memory to execute the instructions to at least: detect an audio signal associated with a patient's breathing with the microphone for a time period; use the audio signal to approximate the patient's respiratory flow for the time period; tag the respiratory flow for the time period with a factor related to the patient; and save the tagged respiratory flow for the time period in a database for future analysis, wherein the tagged respiratory flow for the time period is associated with at least one treatment suggestion. For example, the audio signal can be analyzed by determining a representation of an audio frequency of the audio signal over the time period, splitting the audio frequency of the audio signal over the time period into a plurality of distinct time steps, determining points comprising a weighted mean frequency at each time step, applying a frequency-to-flow rate linear transformation at each time step to approximate the respiratory flow versus time for the time period; and plotting a graphical representation of the respiratory flow versus time for the time period Another aspect of the present disclosure is a method for analyzing a patient's breathing based on audio signals, collected with a mobile device without requiring dedicated equipment, for respiratory function testing. An audio signal associated with the patient's breathing for a time period can be detected with the mobile device and the audio signal can be used to approximate the patient's respiratory flow for the time period. For example, the audio signal can be analyzed by determining a representation of an audio frequency of the audio signal over the time period, splitting the audio frequency of the audio signal over the time period into a plurality of distinct time steps, determining points comprising a weighted mean frequency at each time step, applying a frequency-to-flow rate linear transformation at each time step to approximate the respiratory flow versus time for the time period; and plotting a graphical representation of the respiratory flow versus time for the time period. The respiratory flow for the time period can be tagged with a factor related to the patient and saved in a database for future analysis.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
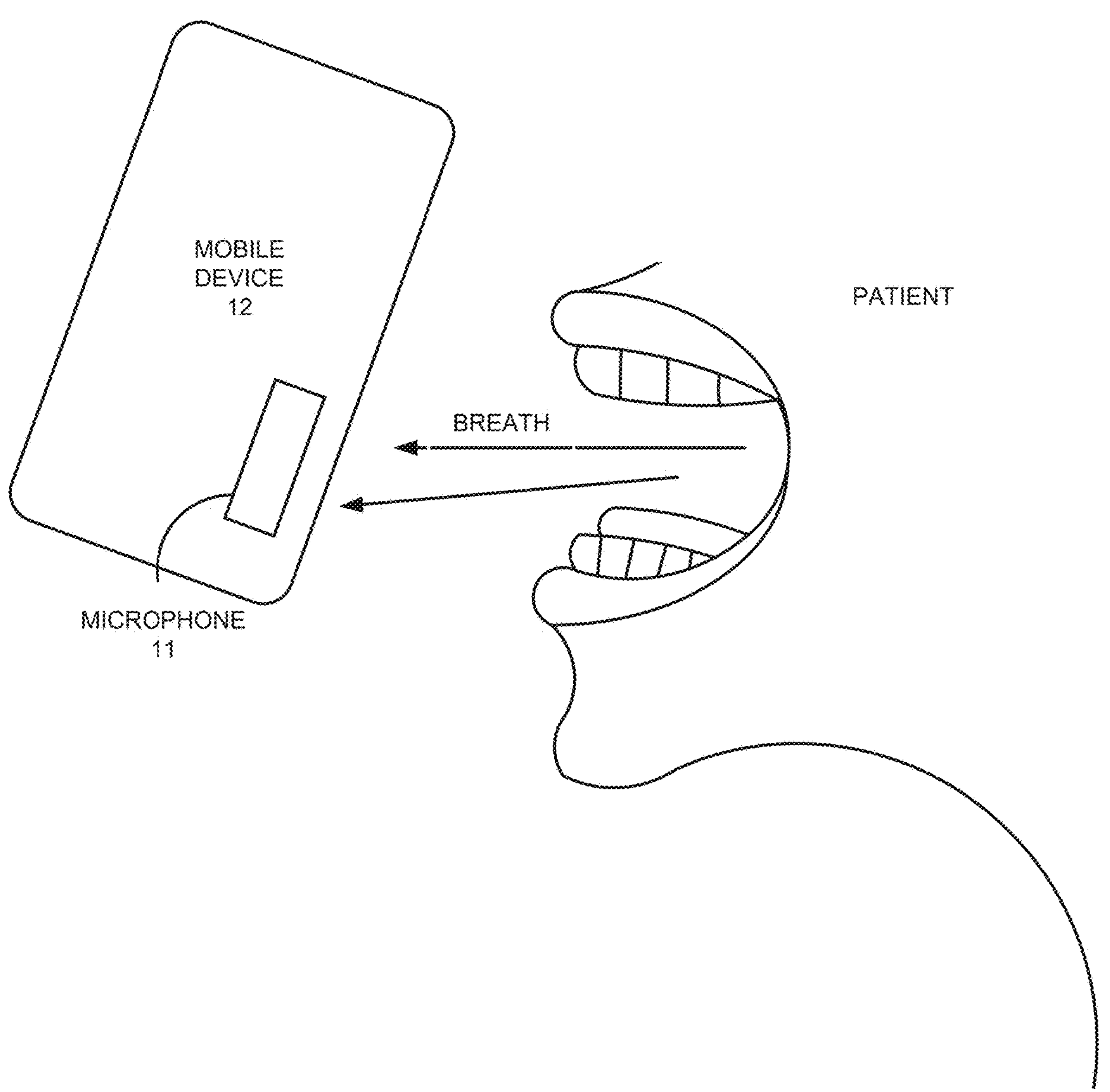
FIG. 1 is an example of using a mobile device to collect audio signals related to a patient's breathing.

Unless otherwise defined, all technical terms used herein have the same meaning as commonly understood by one of ordinary skill in the art to which the present disclosure pertains.

As used herein, the singular forms "a," "an," and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "respiratory function testing" is a subset of pulmonary function testing and generally refers to studying a patient's breathing (respiratory flow for a time period) to identify any defects, disorders, or diseases. Spirometry is one form for respiratory function testing. Respiratory function testing measurements can include, but are not limited to, measurements of FVC, FEV1, FEF values, forced inspiratory flow rates (FIFs), and MVV. Storing measurements of respiratory function testing for a plurality of patients and at a plurality of times can be used to study environmental factors, demographic factors, and clinical factors, including health factors, therapeutic factors, and the like.

As used herein, the term "mobile device" refers to an electronic device, such as a hand-held device, that can be associated with a sound recording capability and access to on-device (e.g., internal processor) or off-device computing (e.g., cloud-based computing) such that the mobile device can at least receive an audio input, perform processing, and provide an output based on the processing. Examples of mobile devices include smartphones, tablet computing devices, laptop computing devices, or the like. In certain instances, a mobile device can be a device that receives an audio input and delivers the input to a separate computing device for further analysis, such as a landline or mobile phone not configured to perform processing. As another example, a mobile device can receive data from an external device (e.g., a smart watch) with various sensors (the external device may also have some level of processing, in some instances). A smart watch is a special case of a device that can be a mobile device in some instances and an external device in other instances (and may be implemented as both a mobile device and an external device together).

As used herein, the term "microphone" refers to an audio-recording device that translates sound vibrations in air into electronic signals (analog or digital) that are recorded. A microphone can be within a mobile device, on a mobile device, or coupled to the mobile device for data transmission.

As used herein, the term "dedicated equipment" refers to traditional pieces of hardware (e.g., a spirometer, a whistle detection device, or the like) that are commonly used to complete respiratory function testing. For example, the dedicated equipment can include devices that take low resolution mechanical measurements and bulky/expensive hospital equipment.

As used herein, the term "audio signal" refers to the representation of sound using a changing (positive and negative) level of electrical voltage (analog) or a series of binary numbers (digital). An audio signal generally is within the audio frequency range corresponding to the lower level of human hearing (about 20 Hz) to the upper level of human hearing (about 20,000 Hz).

As used herein, "audio frequency" refers to a periodic vibration whose frequency is audible to the average human. Generally, the audio frequency is the property of sound that most determines pitch.

As used herein, the term "patient" refers to any warm-blooded organism including, but not limited to, a human being, a pig, a rat, a mouse, a dog, a cat, a goat, a sheep, a horse, a monkey, an ape, a rabbit, a cow, etc. The terms patient and subject can be used interchangeably.

As used herein, the term "individual" refers to a human accessing information in one or more databases. In some instances, the individual may be the patient or a medical professional associated with the patient. However, in other instances, the individual may be a researcher studying trends in data included in the database.

II. Overview

Traditionally, a patient's pulmonary function can be measured with tests such as spirometry (e.g., using a spirometer) to diagnose and monitor conditions such as asthma, COVID-19, bronchitis, chronic obstructive pulmonary disease (COPD), cystic fibrosis, and pulmonary fibrosis. However, the spirometer, and other devices traditionally used for respiratory measurements, often provide low resolution mechanical measurements or require bulky and/or expensive hospital equipment. Thus, it is difficult to acquire accurate data and a high level of data acquisition from one or more patients. Additionally, use of the spirometer, and other devices traditionally used for respiratory measurements, requires significant user compliance with directions (e.g., cannot be used with young children, cannot be used with patients who cannot follow directions, cannot be used with patients who have one or more contraindications, etc.), may not accurately include the effects of environmental triggers (e.g., pollutants, asthma triggers, etc.), and may not accurately account for demographic factors (e.g., does not account for differences for different ethnicities, sexes, etc.). Using a spirometer, and other devices traditionally used for respiratory function testing, often has a significant cost, can take a large amount of time and/or space depending on the tests being run, and has a high user requirement for measurement in which a large amount of effort is required by an individual patient and/or requires a large amount of users to be able to compare measurements so these devices cannot easily be used for large scale respiratory function testing.

Described herein is a solution to provide low cost, large scale respiratory function testing based on audio signals recorded by a mobile device. The mobile device can analyze a patient's breathing based on audio signals detected by a microphone without requiring the purchase of additional dedicated equipment or instruction and monitoring by a medical professional. The lack of required dedicated equipment makes testing more accessible to all demographics and use in any environment and can also lead to the generation of less medical waste. Mobile devices are prevalent through much of the world and can be relatively inexpensive (especially considering their multitudes of uses), thus using mobile devices for respiratory/pulmonary function testing can provide a low cost and easy access alternative to traditional testing methods. Ubiquitous use of mobile phones for pulmonary/respiratory function testing can provide a large amount of new information to databases, corresponding to a large number of patients and situations. Such databases would provide individuals access to health information that could impact long term health and safety, identify impacts that certain environmental factors may have on the health of individuals and communities, and the like.

III. Systems

Audio signals can be used to analyze a patient's breathing for respiratory function testing. A mobile device 12 (shown in FIG. 1) can be used to collect and analyze audio signals from a patient without the need for any extra dedicated equipment or visits to a doctor's office and with a minimal cost, compactness, and ease of use (for patients). After the analysis, the mobile device 12 can further process the result and output a health report/score for the patient For example, the mobile device 12 can produce a vibration or alarm for an asthmatic to use an inhaler if the audio signal so indicates. Additionally, the results of the analysis can be sent to a database and stored for further analysis. As an example, a researcher can access the database to see results of many patients, filter the results by a certain parameter, and analyze the plurality of results.

Mobile devices are highly prevalent throughout much of the world today and can allow for cheap and ubiquitous respiratory health measurements anywhere in the world at any time. If even a small portion of mobile device users used a mobile device for occasional respiratory function testing, then vast quantities of data, that were not previously available, could be collected (e.g., on one or more mobile device(s) 12 or remotely in a database on a cloud or a physical server). The data can be associated with environmental factors (e.g., urbanity of environment, climate, weather, pollution, lifestyle information, effect of exercise, or the like), demographic factors (e.g., gender, age, ethnicity, or the like), clinical factors (e.g., disease state or progression, treatment success, or the like), or other factors, to enable individuals to study of how the various factors affect respiratory health.

As shown in FIG. 1, the mobile device 12 can be a device comprising a microphone 11 that a patient can breathe (exhale and/or inhale) or speak towards. For example, the mobile device 12 can be a hand-held device (such as a smartphone) that can at least receive an audio input (e.g., via the microphone 11), perform processing on the audio input, and provide an output based on the processing. The output can be at least one of a visual display (e.g., on a display of the mobile device 12 or a display associated with the mobile device), an auditory alert (e.g., via a speaker of the mobile device 12 or a speaker associated with the mobile device), or a haptic alert (e.g., through a vibro-tactile mechanism of the mobile device 12). Examples of mobile devices 12 include smartphones, tablet computing devices, laptop computing devices, smart watches, or the like. In certain instances, a mobile device 12 can be a device that receives an audio input and delivers the input to a separate computing device that is in audio or electrical communication with the mobile device for further analysis, such as a landline or mobile phone not configured to perform processing.

Figure 2:
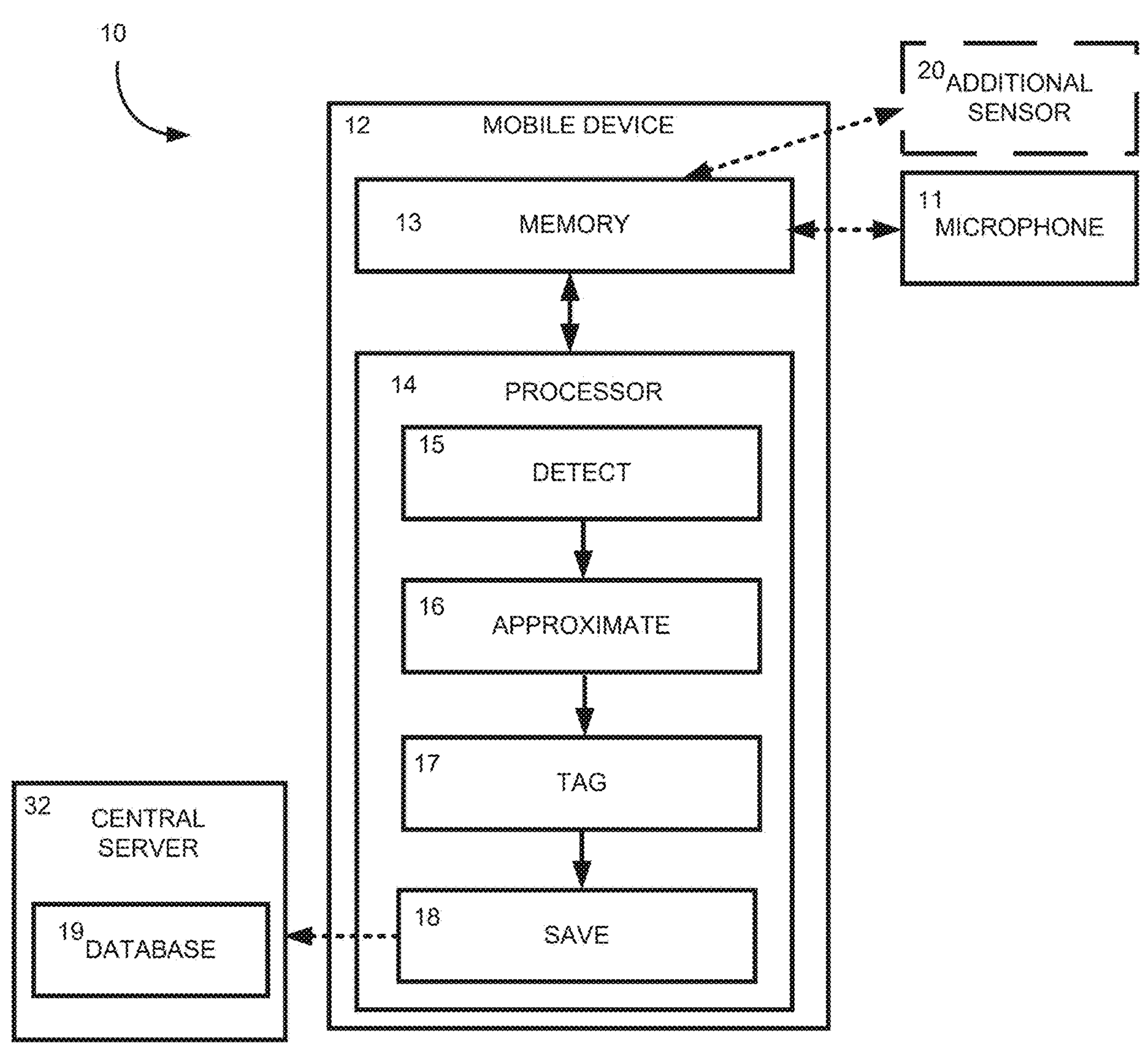
FIG. 2 is a diagram of a mobile device that receives the audio signals collected in the manner of FIG. 1 and analyzes the patient's breathing.

FIG. 2 shows a diagram 10 of an example of mobile device 12 that can include and/or be associated with a microphone 11 for measuring and then processing audio signals of a patient. At a minimum, the microphone 11 can record the audio signals of patient and send the audio signals to the mobile device 12. The microphone 11 can be located within a mobile device 12 (as shown in FIG. 1), on a mobile device 12, and/or coupled to the mobile device 12 for data transmission (shown in FIG. 2) (e.g., wired or wireless headphones or microphone). The microphone 11 can send the audio signals to the mobile device 11 via a wired connection and/or a wireless connection. For example, if the mobile device 12 is a smartphone, then the smartphone can include a microphone and can be connected, wired or wirelessly (e.g., Bluetooth), with headphones worn by a patient. If the headphones are connected than the microphone of the headphones can be configured to receive the audio input rather than the microphone of the smartphone.

The mobile device 12 can, after receiving the audio signals via microphone 11, process the audio signals to measure and analyze the patient's breathing. The mobile device 12 can include a memory 13 (e.g., a non-transitory memory) that can store machine executable instructions and a processor 14 that can be configured to access the memory to execute the instructions. In some instances, the memory 13 and the processor 14 can be merged together and operate as a microprocessor, but in other instances, the memory and the processor can include at least partially distinct hardware elements. The memory 13 can also store data, such as audio signals received from the microphone 11, data from one or more additional sensor 20 and/or the measurements output by the analysis of the audio signals. Upon execution of the instructions, the mobile device 12 can detect 15 an audio signal associated with a patient's breathing (or speech) with the microphone 11 for a time period. The time period can be predefined by a setting on the mobile device 12 and/or by an individual (e.g., a medical professional, an athletic trainer, or a researcher for a clinical trial or other research/study) as a value common for most patients (and may be further classified by age/sex/race/smoker/condition/etc.). The time period can also be patient selected. For example, an athlete can select one time period to provide information about lung fitness, while a smoker can select another time period to provide other information about lung fitness. The time period can be, for example, one second, two seconds, five seconds, ten seconds, thirty seconds, one minute, ten minutes, fifteen minutes, thirty minutes, one hour, or the like.

The mobile device 12 can use the audio signal to approximate 16 the patient's respiratory flow for the time period. The respiratory flow (or at least a portion of the respiratory flow) for the time period can be tagged 17 with a factor related to the patient. For example, the tag can be based on one or more of environmental factors, demographic factors, clinical factors (e.g., disease, treatment, etc.), or other factors, for further analysis. The further analysis can be by the processor 14 of the mobile device 12, the patient, by a medical professional associated with the patient, an individual, or the like. The tagged respiratory flow for the time period can be saved 18 in a database 19 for current or future analysis. In some instances, the tagged respiratory flow for the time period can also be saved in the local memory 13 of the mobile device 12. The database 19 can be located in the memory 13 of the mobile device 12 and/or in a central server 32.

One or more additional sensor 20 can be included in the mobile device 12 (not shown) or external to and associated with the mobile device (as shown in FIG. 2). Examples of the one or more additional sensor 20 internal to or external to (but associated with the mobile device 12 can include, but are not limited to IMU/proximity sensors, GPS, accelerometers, gyroscopes, heart rate sensors, ECG sensors, or SpO2 sensors. In some instances, the one or more additional sensor 20 can be included in a secondary mobile device (not shown) that is associated with a primary mobile device (mobile device 12), such as a smart watch or fitness tracker paired with a smart phone. Readings from the one or more additional sensor 20 can be accessed (via wired and/or wireless communication) for at least the time period the audio signal is detected to be paired with (tagged) the respiratory flow. In some instances, readings from the one or more additional sensor 20 can be used as additional information for approximating 16 the patient's respiratory flow for the time period (e.g., account for distance between the microphone and the patient's mouth, the activity level of the patient, the heart rate of the patient, surrounding extraneous sounds, or the like) and/or tagged to the respiratory flow data.

The processor 14 of the mobile device 12 can also make one or more treatment suggestion based on the respiratory flow data and/or the additional sensor recordings. In some instances, the mobile device 12 can include a display or speaker (not shown) for the visual/audio display of the patient's respiratory flow for the time period, the treatment suggestion, warnings, or the like. Such outputs can also be added as tags to the saved respiratory flow data The mobile device (via a display) can also display the current respiratory flow data and/or pulmonary function measurements in comparison to at least one past respiratory flow data and/or pulmonary function measurements to, for example, track if a treatment is effective, over all respiratory and/or cardiovascular health of the patient, etc.

Figure 3:
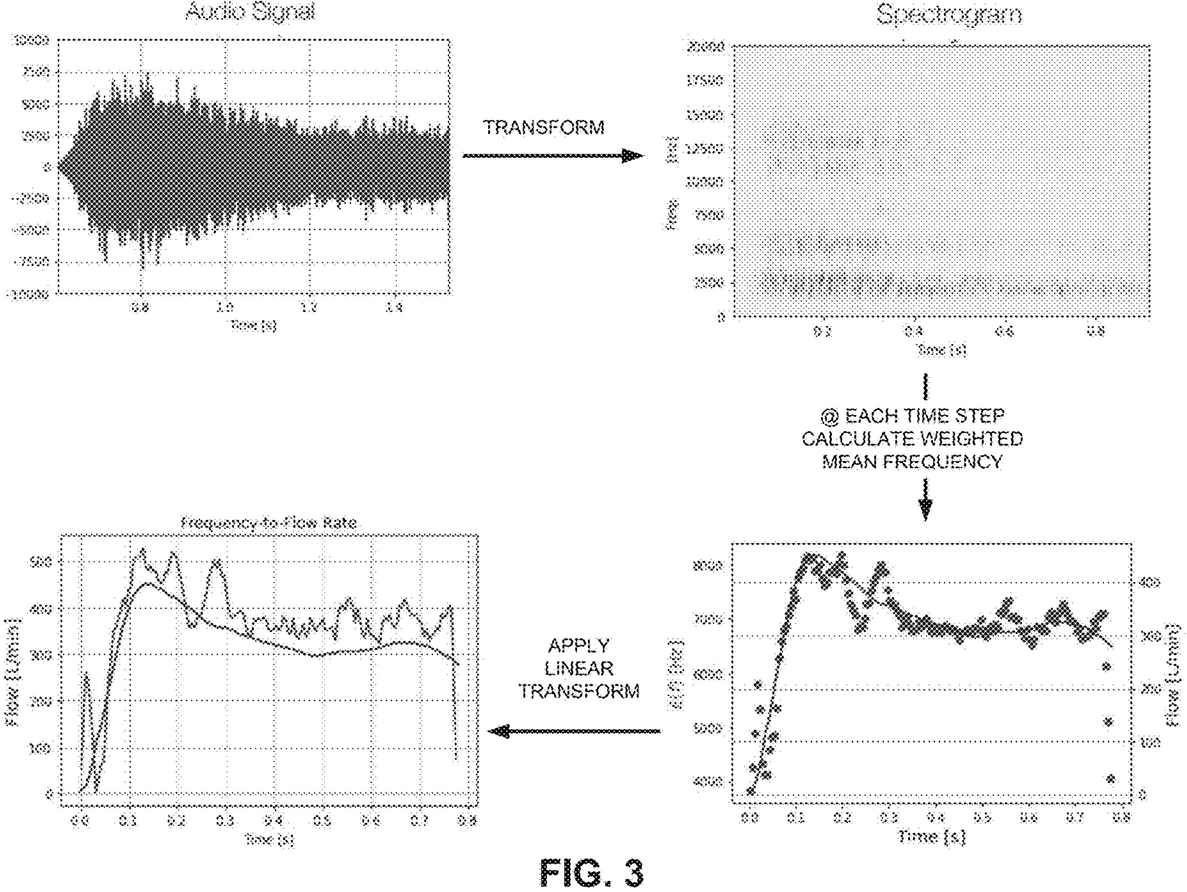
FIG. 3 is an example of how the mobile device of FIG. 2 analyzes the audio signals for respiratory function testing.

An example of how the audio signal can be used by the mobile device 12 to approximate 16 the patient's respiratory flow for the time period is shown in FIG. 3. After an audio signal of the patient's breathing has been detected for a time period a representation of an audio frequency of the audio signal over the time period can be determined. As shown in the graphical representation on the top left of FIG. 3, the audio signal has a changing amplitude of positive and negative values over the time period. The audio frequency of the audio signal over the time period can be split into a plurality of distinct time steps, as shown in the spectrogram on the top right of FIG. 3. For example, the audio signal can be transformed into a spectrogram by applying a Fourier Transform, a Laplace Transform, and/or a Z-transform to the audio signal. Then, at each time step, one or more weighted mean frequencies can be calculated (by the processor 14 of the mobile device 12), as illustrated by the graphical representation on the bottom right of FIG. 3 (with the standard line from a standard test shown for comparison). For example, the mobile device 12 (via the processor 14) can determine one or more points comprising a weighted mean frequency at each time step. The mobile device 12 (via the processor 14 can then apply a frequency-to-flow rate transformation at each time step to approximate the respiratory flow versus time for the time period. In some instances, the transformation can be linear or non-linear. For example, the frequency-to-flow rate transformation can be a linear transformation of the form Flow Rate=A×E(f)−B, where A and B are coefficients that are determined either by population estimates (e.g., based on the weight, height, gender, race, etc.) or calibrated specifically for the individual. The population estimates can be determined based on information provided by the patient before starting to use the mobile device 12. As an example, the frequency-to-flow rate linear transformation can be based on a best fit equation of Flow Rate=0.115×E(f)−423.44, where E(f) is the weighted mean frequency at each of the time steps. A graphical representation of the respiratory flow versus time for the time period, as shown on the bottom left of FIG. 3) can be plotted (with the standard line from a standard test shown for comparison). The graphical representation of the respiratory flow versus time is an approximation of the patient's respiratory flow curve (which during testing purposes was also taken using a traditional spirometer for comparison). The approximation of the respiratory flow of the patient can approximate traditional respiratory flow curves taken with a spirometer or a tube, taken during whistling (Strouhal's number and/or Reynold's number, and the like). It should be understood that graphical representations are shown to illustrate the steps taken and calculations can be completed by the processor 14 of the mobile device 12 without creation and/or display of one or more of the graphical representations.

The processor 14 of mobile device 12 can also, optionally, analyze the patient's respiratory flow for the time period, and/or for multiple time periods to determine respiratory flow measurements of the patient's lung function including: vital capacity (VC), forced vital capacity (FVC), forced expiatory capacity (FEC), forced expiatory volume (FEV) at timed intervals of 0.5, 1.0, 2.0, and 3.0 seconds, forced expiatory flow 25%-75% (FEF 25-75), peak expiratory flow (PEF), maximal expiratory flow when X % remains ($MEF_x$), maximal mid-expiratory rate (MMEF), and maximal voluntary ventilation (MVV)/maximum breathing capacity, etc.). In certain instance one or more of the measurements and/or warnings associated with one or more measurements can be output (via audio, visual, and/or tactile mechanisms) to the patient via the mobile device 12.

Figure 4:
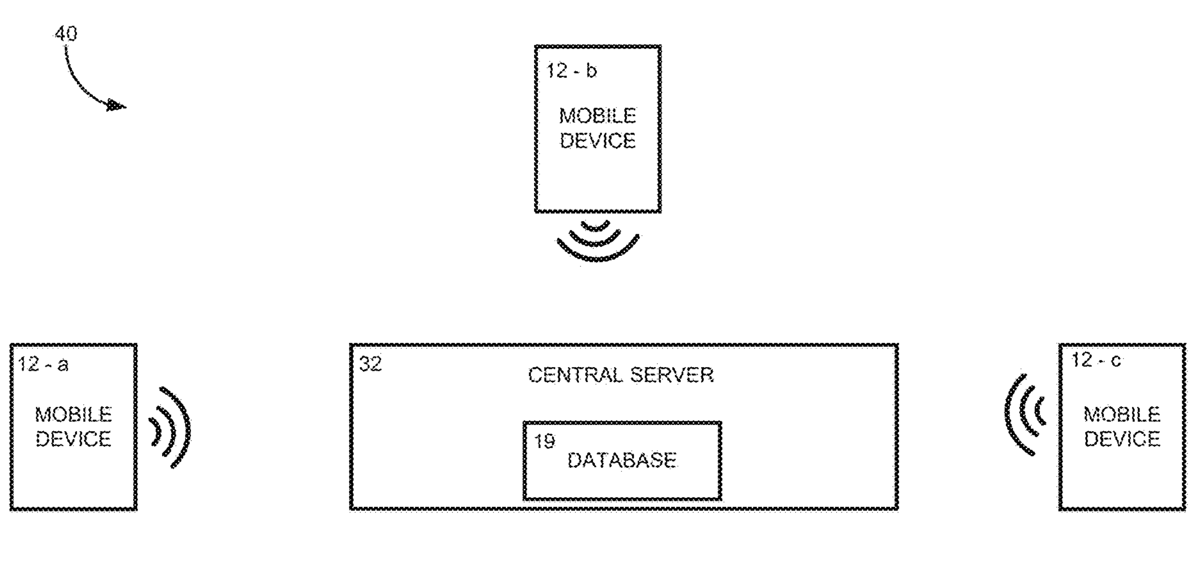
FIG. 4 is a diagram of a plurality of mobile devices of FIG. 2 sending data to a central server.

FIG. 4 displays an example system 40 showing how different mobile devices 12-*a*-12-*n* (of a plurality of patients) can send data, such as tagged respiratory flow and/or measurements derived from a tagged respiratory flow, to a central server 32. The central server 32 can be one or more connected central servers. The central server 32 can receive data over wireless connections (as shown) and/or wired connections. The data can be stored in the database 19 of central server 32 and when accessed can be filtered according to one or more of the tagged factors. The prevalence of mobile devices 12 can lead to a large amount of data being stored in the database 19 associated with a plurality of tags. Individuals (such as medical professionals and/or researchers) can access the database 19 (according to an open us set up, a subscription set up, or the like) and study data having one or more of the various tags.

As an example, the data can be tagged (or geotagged) with health metrics and/or respiratory data for different patients. An individual can query the database 19 for users of a certain age and race at a certain location and be able to study relevant data that is filtered by the certain age and race and the certain location, which could provide insight into environmental, demographic, or therapeutic factors in respiratory health.

IV. Methods

Another aspect of the present disclosure can include methods 50 and 60 (FIGS. 5 and 6) for analyzing the patient's breathing based on audio signals collected with a mobile device (shown, e.g., in FIGS. 1 and 2) without requiring dedicated equipment for respiratory function testing. An example of how the patient's breathing is analyzed is shown in FIG. 3. The mobile device can be, for example, a cellular phone, a smartphone, a landline telephone, a tablet computing device, a laptop computing device, a smart watch, or the like. In some instances, the mobile device can be a smart watch, but a smart watch can additionally or alternatively be an external device with sensors that provides data to the mobile device.

The methods 50 and 60 are illustrate as process flow diagrams with flowchart illustrations. For purposes of simplicity, the methods 50 and 60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50 and 60, nor are methods 50 and 60 limited to the illustrated aspects.

One or more blocks of the respective flowchart illustrations, and combinations of blocks in the flowchart illustrations, can be implemented by computer program instructions. These computer program instructions can be stored in memory and provided to a processor of a mobile device, a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 50 and 60 of the present disclosure may be embodied in hardware and/or in software (including firmware, resident software, micro-code, etc.). As an example, the hardware and/or software can embody or be embodied on a mobile device. Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Figure 5:
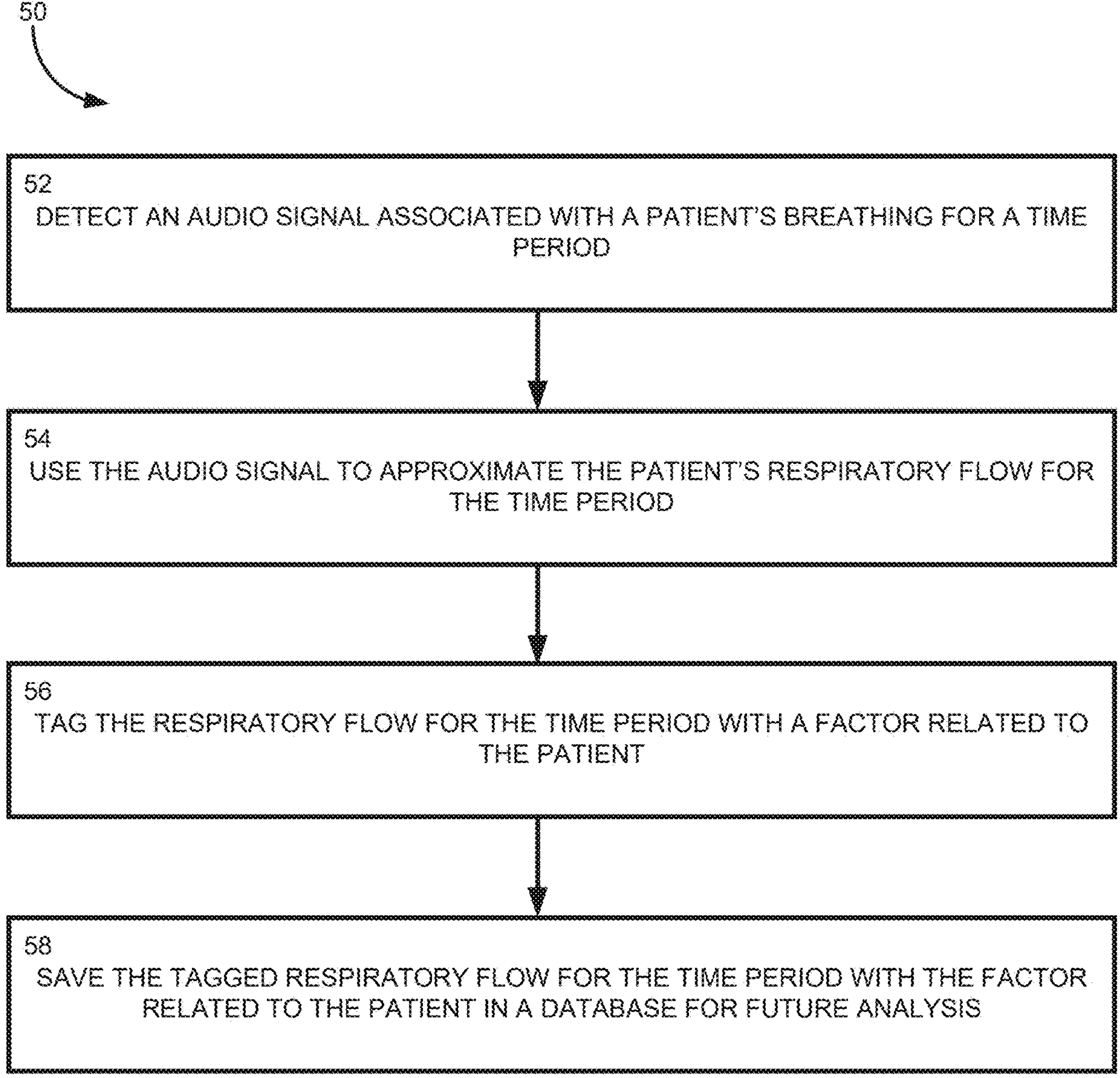
FIGS. 5 and 6 are process flow diagrams of methods for analyzing the patient's breathing based on audio signals collected with a mobile device without requiring dedicated equipment for respiratory function testing.

The method 50 of FIG. 5 uses a mobile device to analyze a patient's breathing. The analysis of FIG. 5 begins at 52, where an audio signal associated with the patient's breathing for a time period is detected (e.g., by a mobile device associated with a microphone, either within the mobile device, on the mobile device, or in electrical communication with the mobile device). The audio signal of the time period can be associated with a patient's normal breathing, speech, whistling, or the like. For example, the audio signal for the time period is generally associated with the patient's normal breathing and can have a changing amplitude including positive and negative values (e.g., shown in FIG. 3, top left). However, it should be understood that the audio signal can take any form. In some instances, the audio signal can be based on whistling in the patient's breathing (e.g., because the throat and mouth of a human can form a first orifice, the tongue and throat, and second orifice, the lips, that can add whistling tones). The time period the breathing of the patient is detected for can be based on the time between a start time and a stop time. The start time and the stop time and/or the time period can be user selected, entered by the user, or according to a predefined time period set by a medical professional or standard for an application. In one example, the time period can be indicative of at least the flow rate of an entire inhalation and/or exhalation of the patient.

At 54, the audio signal can be used by the mobile device to approximate the patient's respiratory flow for the time period. At 56, information associated with the patient's respiratory flow for the time period can be tagged with a factor related to the patient. One or more factors can be tagged to the same respiratory flow information. The factor related to the patient can be, for example, an environmental factor, a demographic factor, a health factor, a therapeutic factor, or the like. In some instances, the mobile device can receive readings from one or more additional sensor (internal to the mobile device and/or external to the mobile device) and/or user inputs. The one or more additional sensor recordings and/or user inputs can be associated with the tagged respiratory data and/or used as additional information for the approximation of the respiratory flow of the patient. The additional sensor recordings and/or user inputs can be saved in the database with the tagged respiratory flow for the time period. The additional sensor recordings can include recordings from an IMU, a proximity sensor, a heart rate sensor, a SpO2 sensor, an ECG sensor, a GPS, an accelerometer, or the like.

At 58, the tagged respiratory flow for the time period can be saved in a database (located locally and/or remotely) for future analysis. A respiratory metric can be extracted (e.g., by a processor of the mobile device, by an individual performing research, a medical professional associated with the patient, or the like) from the respiratory flow for the time period and/or for a plurality of time periods. Examples of the respiratory metric can include force vital capacity, forced expiratory volume in 1 s, peak expiratory flow, maximal expiratory flow when X % remains, maximal mid-expiratory flow, etc.

Additionally, one or more treatment suggestions can be made based on the respiratory flow data and/or the additional sensor recordings. In some instances, the mobile device can include a display or speaker for visual/audio display. Displayed information can include patient's respiratory flow for the time period, the treatment suggestion, warnings, or the like. Such outputs can also be added as tags to the saved respiratory flow data. The mobile device (via a display) can also display the current respiratory flow data and/or pulmonary function measurements in comparison to at least one past respiratory flow data and/or pulmonary function measurements to, for example, track if a treatment is effective, over all respiratory and/or cardiovascular health of the patient, etc.

Figure 6:
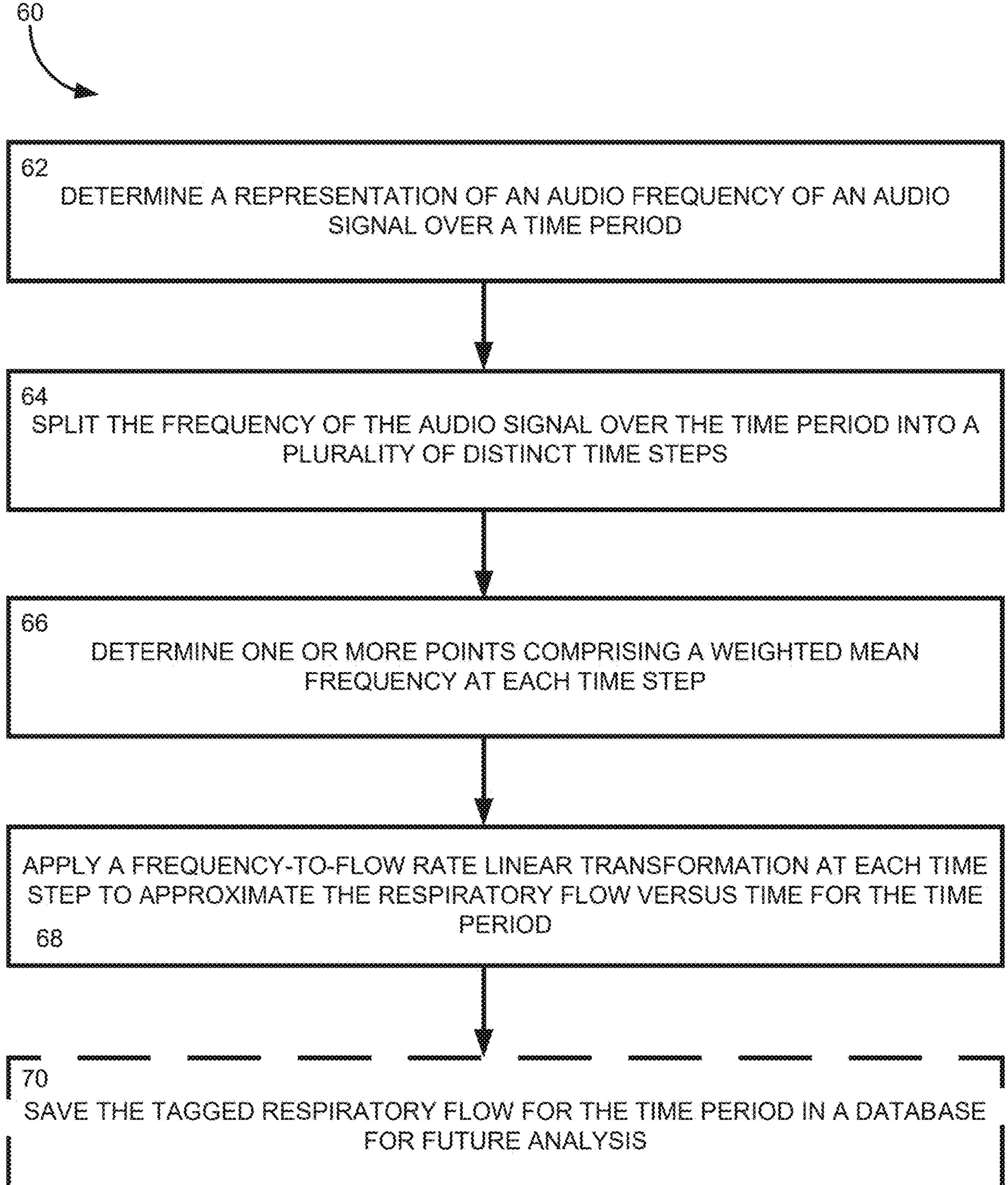

FIG. 6 shows an example method 60 for approximating the respiratory flow for the time period. An illustrated representation of FIG. 6 can be found in FIG. 4. At 62, a representation of an audio frequency of the audio signal over the time period can be determined. For example, the audio signal can include a changing amplitude of positive and negative values over the time period. At 64, the audio frequency of the audio signal over the time period can be split into a plurality of distinct time steps (e.g., by applying a Fourier Transform, a Laplace Transform, and/or a Z-transform to the audio signal). At 66, a weighted mean frequency at each time step can be determined. At 68, a frequency-to-flow rate transformation at each time step can be applied to approximate the respiratory flow versus time for the time period. In some instances, the transformation can be linear or non-linear. For example, the frequency-to-flow rate transformation can be a linear transformation of the form Flow Rate=A×E(f)−B, where A and B are coefficients that are determined either by population estimates (e.g., based on the weight, height, gender, race, etc.) or calibrated specifically for the individual. The population estimates can be determined based on information provided by the patient before starting to use the mobile device. One example of a frequency-to-flow rate linear transformation if performed based on an equation: Flow Rate=0.115×E(f)−423.44, where E(f) is the weighted mean frequency at each of the time steps. However, other equations can be used in the frequency-to-flow rate linear transformation depending on a level of the match, the flow rate (high/low), the reference spirometer, or the like. A graphical representation of the respiratory flow versus time for the time period can be plotted. At 70, the data related to the tagged respiratory flow rate for the time period can be saved in a database for future analysis (e.g., by a researcher or a medical professional).

From the above description, those skilled in the art will perceive improvements, changes, and modifications. Such improvements, changes and modifications are within the skill of one in the art and are intended to be covered by the appended claims.

The following is claimed:

1. A method for using a mobile device to analyze a patient's breathing, the method comprising:

detecting, by the mobile device, an audio signal associated with the patient's breathing for a time period;

using the audio signal, by the mobile device, to approximate the patient's respiratory flow for the time period by:

determining, by the mobile device, a representation of an audio frequency of the audio signal over the time period;

splitting, by the mobile device, the audio frequency of the audio signal over the time period into a plurality of distinct time steps;

determining, by the mobile device, points comprising a weighted mean frequency at each time step; and applying, by the mobile device, a frequency-to-flow rate linear transformation at each time step to approximate the respiratory flow versus time for the time period;

tagging, by the mobile device, the respiratory flow for the time period with a factor related to the patient; and saving, by the mobile device, the tagged respiratory flow for the time period in a database for future analysis.

2. The method of claim 1, further comprising plotting, by the system, a graphical representation of the respiratory flow versus time for the time period.

3. The method of claim 1, wherein the audio signal comprises a changing amplitude of positive and negative values over the time period.

4. The method of claim 1, wherein determining the representation of the audio frequency of the audio signal over the time period further comprises applying a Fourier Transform, a Laplace Transform, and/or a Z-transform to the audio signal.

5. The method of claim 1, wherein the frequency-to-flow rate linear transformation if performed based on an equation: Flow Rate=A×E(f)−B, where E(f) is the weighted mean frequency at each of the time steps and A and B are constants determined based on historical data from the patient and/or a population.

6. The method of claim 1, further comprising extracting, by the mobile device, a respiratory metric from the respiratory flow for the time period.

7. The method of claim 6, wherein the respiratory metric comprises at least one of force vital capacity, forced expiratory volume in 1 s, peak expiratory flow, maximal expiratory flow when X % remains, or maximal mid-expiratory flow.

8. The method of claim 1, wherein the factor related to the patient is at least one of an environmental factor, a demographic factor, a health factor, or a therapeutic factor.

9. The method of claim 1, wherein the time period is indicative of the flow rate of an entire inhalation and/or exhalation.

10. The method of claim 1, wherein the mobile device is a cellular phone, a smartphone, a landline telephone, a tablet computing device, a laptop computing device, or a smart watch.

11. The method of claim 10, wherein the mobile device comprises a microphone and/or is in electrical communication with a microphone.

12. The method of claim 1, further comprising receiving, by the mobile device, additional sensor recordings and/or user inputs and storing the additional sensor recordings and/or user inputs in the database with the tagged respiratory flow for the time period.

13. The method of claim 12, wherein the additional sensor recordings comprise at least one of recordings from an IMU, a proximity sensor, a heart rate sensor, a SpO2 sensor, an ECG sensor, a GPS, or an accelerometer.

14. The method of claim 1, wherein the audio signal associated with the patient's breathing is based on whistling in the patient's breathing.

15. The method of claim 1, wherein the time period is determined based on a start time and a stop time.

16. A mobile device associated with a microphone and comprising:

a memory storing instructions; and a processor configured to access the memory to execute the instructions to at least:

detect an audio signal associated with a patient's breathing with the microphone for a time period;

use the audio signal to approximate the patient's respiratory flow for the time period by:

determining a representation of an audio frequency of the audio signal over the time period, wherein the audio signal comprises a changing amplitude of positive and negative values over the time period, splitting the audio frequency of the audio signal over the time period into a plurality of distinct time steps, determining points comprising a weighted mean frequency at each of the plurality of distinct time steps, applying a frequency-to-flow rate linear transformation at each of the plurality of distinct time steps to approximate respiratory flow versus time for the time period, and plotting a graphical representation of the respiratory flow versus time for the time period;

tag the respiratory flow for the time period with a factor related to the patient;

save the tagged respiratory flow for the time period in a database for future analysis; and provide one or more treatment suggestions for the patient's breathing based on the respiratory flow for the time period.

17. The system of claim 16, wherein the audio frequency of the audio signal over the time period further is determined by the processor by applying a Fourier Transform, a Laplace Transform, and/or a Z-transform to the audio signal.

18. The system of claim 16, wherein the frequency-to-flow rate linear transformation if performed by the processor based on an equation: Flow Rate=$A \times E(f)-B$, where $E(f)$ is the weighted mean frequency at each of the time steps and A and B are constants determined based on historical data from the patient and/or a population.

* * * * *